(12) United States Patent
Snauwaert et al.

(10) Patent No.: US 8,632,514 B2
(45) Date of Patent: Jan. 21, 2014

(54) LAMINATE WITH INDICIA FOR AN ABSORBENT ARTICLE

(75) Inventors: Sofie Gilberte Snauwaert, Koenigstein (DE); Robert René Van Pappelendam, Desingy (FR); Markus Hermann Borbach, Frankfurt (DE)

(73) Assignee: The Procter & Gamble Company, Cincinnati, OH (US)

( * ) Notice: Subject to any disclaimer, the term of this patent is extended or adjusted under 35 U.S.C. 154(b) by 430 days.

(21) Appl. No.: 13/103,486

(22) Filed: May 9, 2011

(65) Prior Publication Data

US 2011/0213323 A1 Sep. 1, 2011

Related U.S. Application Data

(63) Continuation of application No. 11/477,510, filed on Jun. 29, 2006, now Pat. No. 7,982,090.

(30) Foreign Application Priority Data

Jun. 29, 2005 (EP) .................................. 05014021

(51) Int. Cl.
*A61F 13/514* (2006.01)

(52) U.S. Cl.
USPC ...................................... 604/385.01; 604/358

(58) Field of Classification Search
USPC ............................................. 604/385.01, 358
See application file for complete search history.

(56) References Cited

U.S. PATENT DOCUMENTS

| | | |
|---|---|---|
| 3,759,261 A | 9/1973 | Wang |
| 3,860,003 A | 1/1975 | Buell |
| 4,246,307 A | 1/1981 | Trautwein |
| 4,834,735 A | 5/1989 | Alemany et al. |
| 5,037,416 A | 8/1991 | Allen et al. |
| 5,151,092 A | 9/1992 | Buell et al. |
| 5,269,775 A | 12/1993 | Freeland et al. |
| 5,458,590 A | 10/1995 | Schleinz et al. |
| 5,503,076 A | 4/1996 | Yeo |
| 5,561,863 A | 10/1996 | Carlson, II |
| 5,569,234 A | 10/1996 | Buell et al. |
| 5,650,222 A | 7/1997 | Desmarais et al. |
| 5,766,212 A | 6/1998 | Jitoe et al. |
| 5,830,548 A | 11/1998 | Andersen et al. |
| 5,897,541 A | 4/1999 | Uitenbroek et al. |
| 6,004,306 A | 12/1999 | Robles et al. |
| 6,112,797 A | 9/2000 | Colson et al. |
| 6,142,985 A | 11/2000 | Feist |
| 6,245,168 B1 | 6/2001 | Coenen et al. |
| 6,719,742 B1 | 4/2004 | Mccormack et al. |

(Continued)

FOREIGN PATENT DOCUMENTS

| | | |
|---|---|---|
| EP | 1147755 B1 | 9/2009 |
| WO | WO-2004/050970 A2 | 6/2004 |

*Primary Examiner* — Susan Su

(74) *Attorney, Agent, or Firm* — William E. Gallagher

(57) ABSTRACT

The present invention relates to an absorbent article comprising a liquid impervious backsheet formed from a laminate. The liquid impervious backsheet may include at least three layers, a first layer forming the wearer facing side of the backsheet, a second layer forming the garment facing side of the backsheet, and a third layer partially but not fully covering the garment facing surface of the second layer. The first layer may include at least one first indicium on a garment-facing surface thereof and only present on a front half of the backsheet, the at least one first indicium being visible through said second and third layers when looking at the absorbent article from the garment facing side of backsheet.

8 Claims, 3 Drawing Sheets

(56) References Cited

U.S. PATENT DOCUMENTS

| | | |
|---|---|---|
| 6,733,483 B2 | 5/2004 | Raufman et al. |
| 6,949,689 B2 | 9/2005 | Noda et al. |
| 7,160,600 B2 | 1/2007 | Shepard et al. |
| 7,205,041 B2 | 4/2007 | Nair et al. |
| 7,378,130 B2 | 5/2008 | Coronado et al. |
| 7,662,137 B2 | 2/2010 | Sayama et al. |
| 7,766,890 B2 | 8/2010 | Ito et al. |
| 2001/0031954 A1 | 10/2001 | Jordan et al. |
| 2004/0122398 A1 | 6/2004 | Schnabel et al. |
| 2008/0131657 A1 | 6/2008 | Bauer et al. |
| 2009/0280274 A1 | 11/2009 | Hertlein |

LAMINATE WITH INDICIA FOR AN ABSORBENT ARTICLE

CROSS REFERENCE TO RELATED APPLICATION

This application is a continuation of application Ser. No. 11/477,510, filed Jun. 29, 2006, the substance of which is incorporated herein by reference.

FIELD OF THE INVENTION

The present invention relates to laminates and to absorbent articles, such as diapers and sanitary napkins. More specifically, the present invention relates to multi-layer laminates comprising indicia, absorbent articles comprising such laminates as chassis components and to a method of manufacturing such laminates.

BACKGROUND OF THE INVENTION

Disposable absorbent articles are broadly available and consumers are used to a high performance for the collecting and retaining of menses (in the case of sanitary napkins or panty liners) or for the collecting and retaining urine, and fecal material (in the case of e.g. disposable diapers). From such articles consumers expect a superior absorbency behavior and at the same time expect easy and intuitive handling and reliable fit.

Often, such articles comprise multiple absorbent members, at least one member being primarily designed to store liquid, and at least one other member primarily designed to acquire and/or distribute liquid, the members typically being encapsulated between a topsheet (on the wearer facing side) and a backsheet (on the garment facing side).

The topsheet and the backsheet are essential components of the chassis. The chassis ensures that the absorbent members are held in those places where they can provide their functionality. It is important that the chassis is easy to handle, and allows for easy attachment/pulling-on of the article and easy removal of the article. The chassis, and largely the backsheet, also helps to ensure, that no leakage occurs. Further, the chassis will largely influence the sensory appearance of the diaper, as most of the absorbent members can neither be seen nor touched.

Many attempts in the field are concerned with improving the chassis of an absorbent article: US 2003/0207091 A1 discloses disposable garments provided with graphic designs. The invention is further directed to an ink-printed substance web and a method for making such web. The invention is concerned with alleviating the problem of ink rub-off from ink-printed substrates. It is disclosed to coat the ink-printed substrate with a coating composition to form coating film on the ink film and to form a cross-linked structure between the ink composition and the coating composition.

U.S. Pat. No. 6,733,483 discloses a diaper comprising a front waist area that carries a first indicium for facilitating proper positioning of securement members, which can be in the form of fastener tapes, and wherein the fastener tapes, carrying a second indicium. The first indicium is preferably positioned generally on the backsheet outer surface or on a landing zone member joined to the backsheet. The indicia, which form part of the invention, can be provided of a surface printing, decals applied, to the diapers, embossments or texturing of respective surfaces of the diaper, attachments to the surfaces of the diaper, raised elements extending out from the surface of the diaper and the like. The first and second indicia according to this invention compliment each other and are provided to facilitate the proper and symmetrical application of the diaper to the wearer for maximum comfort and for optimal functioning of the diaper.

WO 2004/05 0970 A2 discloses a printed loop fabric with improved graphic visibility and clarity which may be used for the female portion of a mechanical closure system. In particular, a printed loop fabric is disclosed, which is obtained by a process of flexographic printing of the face of the fabric, and therefore providing improved clarity and visibility of the printed fabrics. In an alternative embodiment a printed loop fabric may be obtained by applying a thermoplastic material to the backside of the loop fabric and printing on the thermoplastic material.

However, there is still a need for improved laminate comprising indicia. Likewise, there is still an unmet need for an absorbent article incorporating such laminate, preferably as its backsheet. Also, there is still an unmet need for better and more accurate manufacturing methods.

It is one objective of the present invention to provide a versatile laminate with indicia, which is useful in absorbent article, particularly as a backsheet of such an article.

It is a further objective to provide a laminate or an absorbent article comprising indicia which are clearly visible and recognizable.

It is one objective of the present invention to provide a versatile laminate with indicia, the laminate comprising three layers, wherein the third layer displays indicia, but can still be adapted to meet multiple functional requirements.

It is one objective of the present invention to provide an absorbent article, which is comfortable to wear and easy and intuitive to attach/pull-on and remove.

Moreover, it is an objective of the present invention to provide a laminate and an absorbent article, which are easy to manufacture and which is suitable for accurate, but low cost mass production.

Moreover, it is an objective of the present invention to provide an absorbent article which and has highly reliable fastening means. These fastening means should neither fail due to improper attachment to matching fastening components by the user, nor due to improper attachment to other portions of the chassis in the manufacturing process.

Even further objectives of the present invention will become apparent from the following description.

SUMMARY OF THE INVENTION

The present invention relates to laminates and to absorbent articles, such as diapers and sanitary napkins, and production methods thereof. Specifically, the present invention is directed to an absorbent article (20) comprising an absorbent core (28) which is covered by a liquid pervious topsheet (24) on the wearer facing side of the core (28) and a liquid impervious backsheet (26) on the garment facing side of the core (28), the liquid impervious backsheet (26) having a longitudinal centerline and a transverse centerline, the transverse centerline defining a front half of the liquid impervious backsheet (26) and a rear half of the liquid impervious backsheet (26), the liquid impervious backsheet (26) also having a garment-facing side and a wearer-facing side, the liquid impervious backsheet (26) comprising at least three layers, a first layer (210) being comprised by the wearer facing side of the liquid impervious backsheet (26) and a second layer (220) being comprised by the garment facing side of the liquid impervious backsheet (26), the first layer (210) comprising a wearer-facing surface and a garment facing surface, the garment facing surface of the first layer (210) of the liquid impervious backsheet (26) comprises at least first indicia (250), said first indicia (250) being present in the front half of the liquid impervious backsheet (26) and said first indicia (250) not being present in the rear half of the liquid impervious backsheet (26), the second layer (220) of the liquid impervious backsheet (26) is provided from a woven or non-woven material, the liquid impervious backsheet (26) comprising a third layer (230) which is provided from a woven or non-woven material and the third layer (230) being comprised by the front half of the backsheet (26) thereby partially but not fully covering the garment facing surface of the second layer (220) of the liquid impervious backsheet (26) and the third layer (230) at least partially covering said first indicia (250), wherein the second and the third layer (230) in combination are translucent as to allow such that said first indicia (250) comprised by said first layer (210) are visible through said second and third layer (230) when looking at the absorbent article from the garment facing side of liquid impervious backsheet (26).

The present invention is also directed to a laminate (200) and to a method of providing a laminate (200) useful as a liquid impermeable backsheet for an absorbent article, the laminate (200) comprising a first, a second, and a third layer (230), the first layer (210) having a first and a second surface, the second layer (220) having a first and a second surface, the third layer (230) having a first and a second surface, wherein the second surface of the first layer (210) faces the first surface of the second layer (220) and the second surface of the second layer (220) faces the first surface of the third layer (230), the first surface of the third layer (230) not fully covering the second surface of the second layer (220), the second surface of the first layer (210) comprising indicia (250), the method comprising a step of combining the first and the second layer (220), the method comprising a step of combining the second and the third layer (230), wherein the step of combining the second layer (220) and the third layer (230) employs an optical placement controller as to combine the second layer (220) and the third layer (230) such that the first surface (231) of the third layer (230) is placed in a selected position onto the second surface (222) of the second layer (220), the optical placement controller employing an optical signal received from the indicia (250) comprised by the second surface (212) of the first layer (210).

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

DETAILED DESCRIPTION OF THE INVENTION

Definitions

Figure 1:
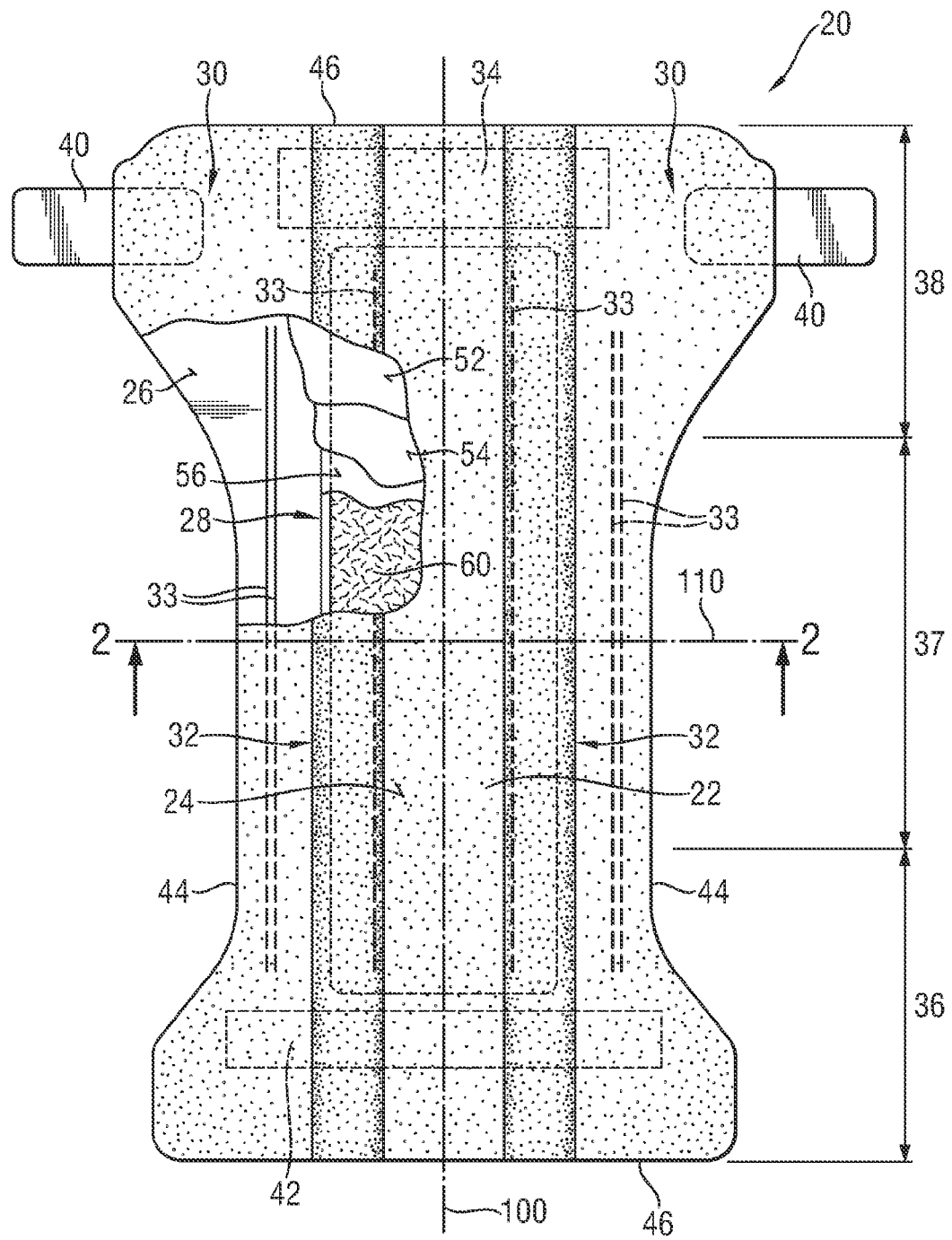
FIG. 1 is a top plan view of a disposable diaper, with the upper layers partially cut away.

As used herein, the following terms have the following meanings:

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers, adult incontinent briefs, training pants, diaper holders and liners, sanitary napkins and the like. Absorbent articles also include wipes, such as household cleaning wipes, baby wipes, and the like.

"Disposable" is used herein to describe articles that are generally not intended to be laundered or otherwise restored or reused i.e., they are intended to be discarded after a single use and, preferably, to be recycled, composted or otherwise disposed of in an environmentally compatible manner.

"Disposed" is used to mean that an element(s) is formed (joined and positioned) in a particular place or position as a unitary structure with other elements or as a separate element joined to another element.

"Diaper" refers to an absorbent article generally worn by infants and incontinent persons about the lower torso.

The terms "thickness" and "caliper" are used herein interchangeably.

"Attached" or "Joined" encompasses configurations whereby an element is directly secured to another element by affixing the element directly to the other element, and configurations whereby an element is indirectly secured to another element by affixing the element to intermediate member(s) which in turn are affixed to the other element.

"Comprise," "comprising," and "comprises" is an open ended term that specifies the presence of what follows e.g. a component but does not preclude the presents of other features, elements, steps or components known in the art, or disclosed herein.

The term "hydrophilic" describes fibers or surfaces of fibers, which are wetable by aqueous fluids (e.g. aqueous body fluids) deposited on these fibers. Hydrophilicity and wetability are typically defined in terms of contact angle and the strike through time of the fluids, for example through a nonwoven fabric. This is discussed in detail in the American Chemical Society publication entitled "Contact angle, wetability and adhesion", edited by Robert F. Gould (Copyright 1964). A fiber or surface of a fiber is said to be wetted by a fluid (i.e. hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be hydrophobic if the contact angle is greater than 90° and the fluid does not spread spontaneously across the surface of the fiber.

The terms "fiber" and "filament" are used interchangeably.

The terms "nonwoven", "nonwoven fabric" and "nonwoven web" are used interchangeable. The disposable article 20 has two centerlines, a longitudinal centerline 100 and a transverse centerline 110.

The term "longitudinal", as used herein, refers to a line, axis or direction in the plane of the disposable article 20 that is generally aligned with (e.g., approximately parallel to) a vertical plane which bisects a standing wearer into left and right body halves when the disposable article 20 is worn.

The terms "transverse" or "lateral" as used herein, are interchangeable, and refer to a line, axis or direction which lies in the plane of the disposable article 20 that is generally perpendicular to the longitudinal direction.

Absorbent Articles

FIG. 1 is a plan view of a diaper 20 as a preferred embodiment of an absorbent article according to the present invention. The diaper is shown in its flat out, uncontracted state (i.e., without elastic induced contraction). Portions of the structure are cut away to more clearly show the underlying structure of the diaper 20. The portion of the diaper 20 that contacts a wearer is facing the viewer. The chassis 22 of the diaper 20 in FIG. 1 comprises the main body of the diaper 20. The chassis 22 comprises an outer covering including a liquid pervious topsheet 24 and/or a liquid impervious backsheet 26. The chassis may also include most of, or the entire absorbent core 28 encased between the topsheet 24 and the backsheet 26. The chassis preferably further includes side panels 30, leg cuffs 32 and a waist feature 34. The leg cuffs and the waist feature typically comprise elastic members 33. One end portion of the diaper 20 is configured as the front waist region 36 of the diaper 20. The opposite end portion is configured as the rear waist region 38 of the diaper 20. An intermediate portion of the diaper 20 is configured as the crotch region 37, which extends longitudinally between the front and rear waist regions 36 and 38. The crotch region 37 is that portion of the diaper 20 which, when the diaper 20 is worn, is generally positioned between the wearer's legs. The waist regions 36 and 38 may include a fastening system comprising fastening members 40 preferably attached to the rear waist region 38 and a landing zone 42 attached to the front waist region 36. The diaper 20 has a longitudinal axis and centerline 100 and a transverse axis and centerline 110. The periphery of the diaper 20 is defined by the outer edges of the diaper 20 in which the longitudinal edges 44 run generally parallel to the longitudinal axis 100 of the diaper 20 and the end edges 46 run generally parallel to the transverse axis 110 of the diaper 20.

For unitary absorbent articles, the chassis 22 comprises the main structure of the diaper with other features added to form the composite diaper structure. While the topsheet 24, the backsheet 26, and the absorbent core 28 may be assembled in a variety of well-known configurations, preferred diaper configurations are described generally in U.S. Pat. No. 5,569,234 entitled "Disposable Pull-On Pant" issued to Buell et al. on Oct. 29, 1996; and U.S. Pat. No. 6,004,306 entitled "Absorbent Article with Multi-Directional Extensible Side Panels" issued to Robles et al. on Dec. 21, 1999.

The topsheet 24 in FIG. 1 may be fully or partially elasticized or may be foreshortened to provide a void space between the topsheet 24 and the absorbent core 28. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The backsheet 26 in FIG. 1 is generally the portion of the diaper 20 positioned with the absorbent core 28 between the backsheet 26 and the topsheet 24. The backsheet 26 may be joined with the topsheet 24. The backsheet 26 prevents the exudates absorbed by the absorbent core 28 and contained within the article 20 from soiling other external articles that may contact the diaper 20, such as bed sheets and undergarments. In preferred embodiments, the backsheet 26 is substantially impervious to liquids (e.g., urine) and comprises a laminate, made of at least a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE.

The absorbent core 28 in FIG. 1 generally is disposed between the topsheet 24 and the backsheet 26. The absorbent core 28 may comprise any absorbent material that is generally compressible, conformable, non-irritating to the wearer's skin, and capable of absorbing and retaining liquids such as urine and other certain body exudates. The absorbent core 28 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminate (200)s, absorbent foams, absorbent sponges, superabsorbent polymers, absorbent gelling, materials, or any other known absorbent material or combinations of materials. The absorbent core may further comprise minor amounts (typically less than 10%) of non-liquid absorbent materials, such as adhesives, waxes, oils and the like.

Exemplary absorbent structures for use as the absorbent assemblies are described in U.S. Pat. No. 4,834,735, entitled "High Density Absorbent Members Having Lower Density and Lower Basis Weight Acquisition Zones", issued to Alemany et al, on May 30, 1989; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997.

The diaper 20 may also include such other features as are known in the art including front and rear ear panels, waist cap features, elastics and the like to provide better fit, containment and aesthetic characteristics. Such additional features are well known in the art and are described in U.S. Pat. No. 3,860,003 entitled "Contractable side portions for disposable diaper" issued to Buell et al, on Jan. 14, 1975 and U.S. Pat. No. 5,151,092 entitled "Absorbent article with dynamic elastic waist feature having a predisposed resilient flexural hinge" issued to Buell et al. on Sep. 29, 1992.

In order to keep the diaper 20 in place about the wearer, the waist regions 36 and 38 may include a fastening system comprising fastening members 40 preferably attached to the rear waist region 38. In a preferred embodiment the fastening system further comprises a landing zone 42 attached to the front waist region 36. (The landing zone 42 may be integral with the backsheet (26).) Preferred fastening systems are adhesive fastening systems and mechanical fastening systems. Preferred mechanical fastening systems comprise, a male and a female component, preferably in the form of hook and loop elements. Therein, the landing zone 42 acts as the female fastening component. The fastening member is attached to the front waist region 36, preferably to the landing zone 42 to form leg openings and an article waist.

Diapers 20 according to the present invention may be provided with a re-closable fastening system or may alternatively be provided in the form of pant-type diapers.

The fastening system and any component thereof may include any material suitable for such a use, including but not limited to plastics, films, foams, nonwoven webs, woven webs, paper, laminates, fiber reinforced plastics and the like, or combinations thereof. It may be preferable that the materials making up the fastening device be flexible. The flexibility is designed to allow the fastening system to conform to the shape of the body and thus, reduces the likelihood that the fastening system will irritate or injure the wearer's skin.

Figure 2:
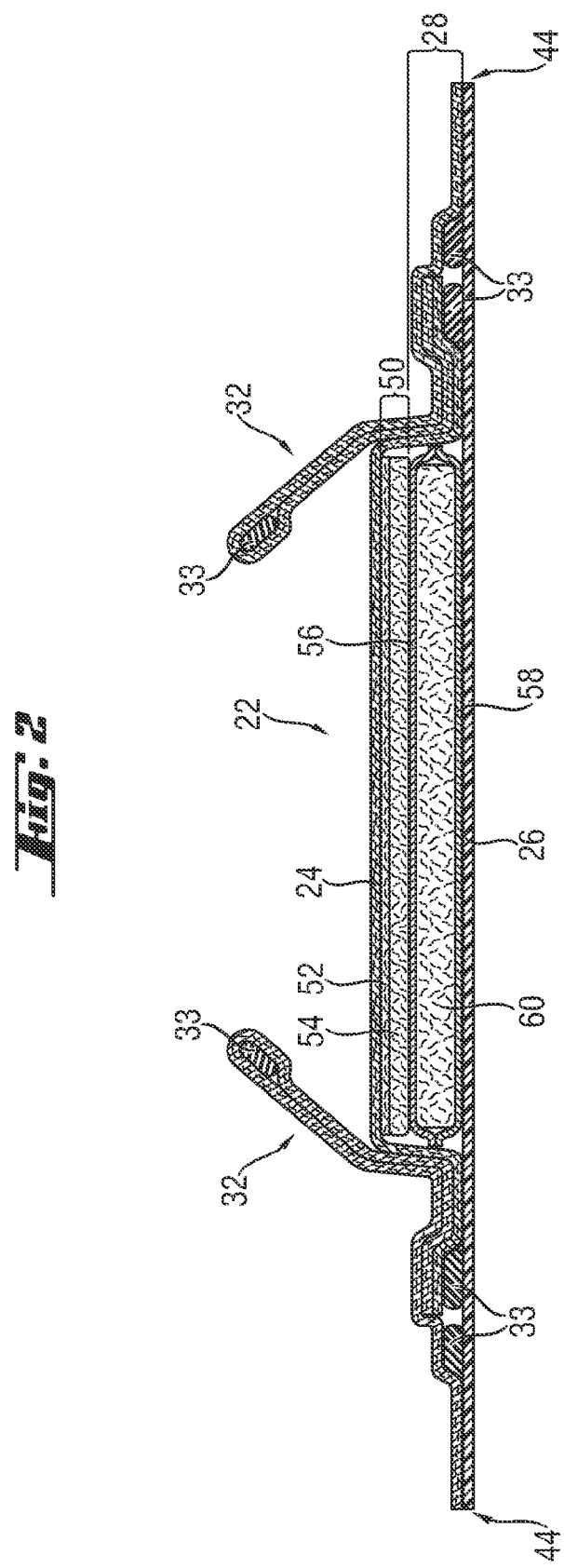
FIG. 2 is a cross-sectional view of the disposable diaper shown in FIG. 1.
Figure 3:
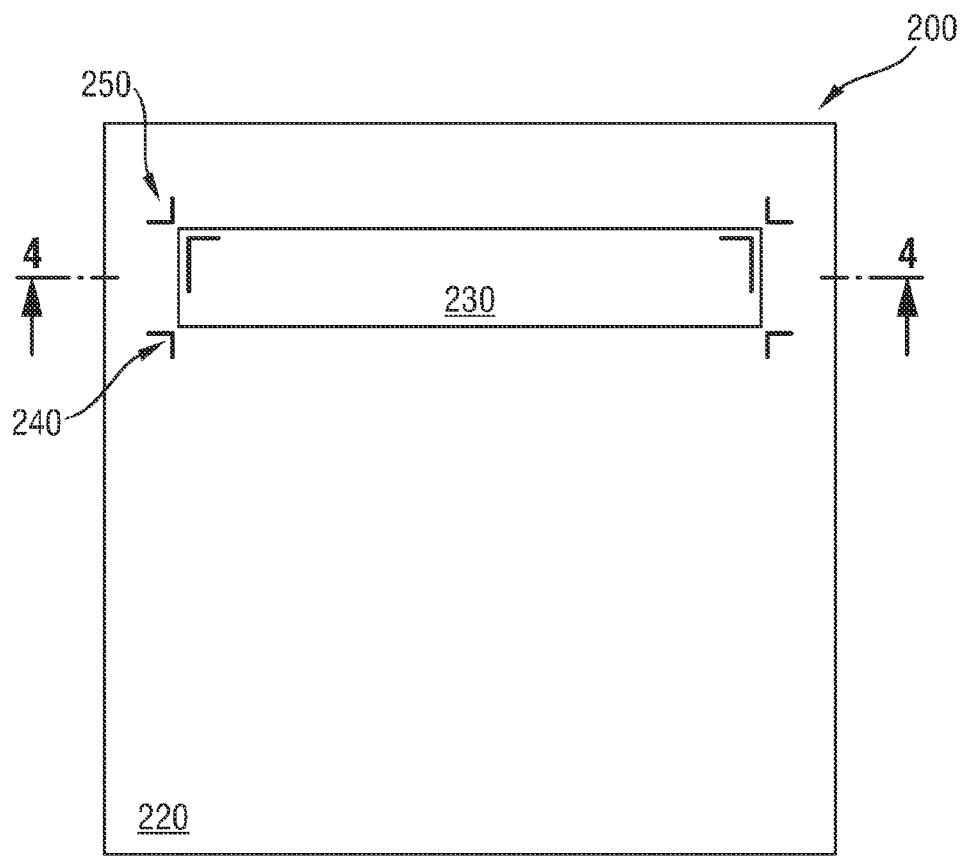
FIG. 3 is a top plan view of a laminate (200) according to the present invention.
Figure 4:
FIG. 4 is a cross-sectional view along line 4-4 of FIG. 3.

FIG. 2 shows a cross-sectional view of FIG. 1 taken in the transverse axis 110. Starting from the wearer facing side the diaper comprises the topsheet 24, the components of the absorbent core 28, and the backsheet 26. The absorbent core preferably comprises an acquisition system 50, which comprises an upper acquisition layer 52 facing towards the wearer and a lower acquisition layer 54. In one preferred embodiment the upper acquisition layer comprises a nonwoven fabric whereas the lower acquisition layer preferably comprises a mixture of chemically stiffened, twisted and curled fibers, high surface area fibers and thermoplastic binding fibers. In another preferred embodiment both acquisition layers are provided from a non-woven material, which is preferably hydrophilic. The acquisition layer preferably is in direct contact with the storage layer 60.

The storage layer 60 is preferably wrapped by a core wrap material. In one preferred embodiment the core wrap material comprises a first core wrap layer 56 (top layer) and a second core wrap layer 58 (bottom layer). The first core wrap layer 56 and the second core wrap layer 58 can be provided from a non-woven material. One preferred material is a so-called SMS material, comprising a spunbonded, a melt-blown and a further spunbonded layer. The first core wrap layer 56 and the second core wrap layer 58 may be provided from two or more separate sheets of materials or they may be alternatively provided from a unitary sheet of material. Such a unitary sheet of material may be wrapped around the storage layer 60, e.g. in a C-fold. The first core wrap layer 56 and the second core wrap layer 58 may also be joined to each other, preferably along their periphery. In one preferred option both layers are joined along their longitudinal peripheries, in other embodiments they are joined along the transversal peripheries, or along the longitudinal and the transversal peripheries. The joining can be achieved my multiple means well known in the art, eg. by adhesive means, using a continuous or a discontinuous pattern, and preferably a linear or curvilinear pattern.

The storage layer 60 typically comprises fibrous materials, mixed with superabsorbent, absorbent gelling materials. Other materials described above as suitable for the absorbent core 28 may also be comprised. Preferred storage layer according to the present invention may comprise a superabsorbent material in an amount corresponding to at least 30%, or at least 40%, or at least 50%, or at least 60%, or at least 70%, or at least 80% or at least 90% of the total weight of the storage layer.

An upper liquid acquisition layer 52 useful in a diaper according to the present invention may comprise any of the nonwoven fabrics described below. A preferred liquid acquisition layer 52 comprises a binder comprising a styrene-butadiene latex binder. Preferably, the styrene-butadiene latex binder has a carboxylation level of at least 10%, preferably at least 12%. Preferably, the upper liquid acquisition layer 52 comprises polyester fibers and the liquid acquisition layer comprises 20 to 40 weight percent of styrene-butadiene latex binder, and 60 to 80 weight percent of said polyester fibers. Even more preferably, the polyester fibers comprise 20 to 80 weight percent of a first type of fibers, and 20 to 80 weight percent of a second type of fibers, the second type of fibers comprising spiral-crimp fibers. Highly preferred are upper liquid acquisition layers wherein the first type of fibers exhibits as flat crimp and wherein the second type of fibers comprises hollow chemically homogeneous bi-component fibers. Also highly preferred are any upper liquid acquisition layers wherein the polyester fibers are carded to form a nonwoven.

Preferred acquisition systems may also comprise superabsorbent materials. Such acquisition systems may also comprise a single acquisition layer or multiple acquisition layers. Where multiple acquisition layers are comprised any of these layer may comprise superabsorbent materials. Such superabsorbent material may be comprised in an amount corresponding to at least 30%, or at least 50% or at least 70%, at times even in an amount of 100% of the total weight of the respective acquisition layer.

Nonwoven Fabrics

A nonwoven fabric is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled.

The fibers may be of natural or man-made origin. They may be staple or continuous filaments or be formed in situ.

Nonwoven fabrics can be formed by many processes such as meltblowing, spunbonding, carding. The basis weight of nonwoven fabrics is usually expressed in grams per square meter (gsm).

Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Fibers are classified according to their origin, chemical structure, or both. They can be braided into ropes and cordage, made into felts (also called nonwovens or nonwoven fabrics), woven or knitted into textile fabrics, or, in the case of high-strength fibers, used as reinforcements in composites—that is, products made of two or more different materials.

The nonwoven fabrics may comprise fibers made by nature (natural fibers), made by man (synthetic or man-made), or combinations thereof. Example natural fibers include but are not limited to: animal fibers such as wool, silk, fur, and hair; vegetable fibers such as cellulose, cotton, flax, linen, and hemp; and certain naturally occurring mineral fibers. Synthetic fibers can be derived from natural fibers or not. Example synthetic fibers, which are derived from natural fibers, include but are not limited to rayon and lyocell, both of which are derived from cellulose, a natural polysaccharide fiber. Synthetic fibers, which are not derived from natural fibers, can be derived from other natural sources or from mineral sources. Example synthetic fibers not derived from natural sources include but are not limited to polysaccharides such as starch. Example fibers from mineral sources include but are not limited to polyolefin fibers such as polypropylene, polyethylene fibers and polyester, which are derived from petroleum, and silicate fibers such as glass and asbestos.

Nonwoven webs can be formed by direct extrusion processes during which the fibers and webs are, formed at about the same point in time, or by preformed fibers, which can be laid into webs at a distinctly subsequent point in time. Example direct extrusion processes include but are not limited to: spunbonding, meltblowing, solvent spinning, electrospinning, and combinations thereof typically forming layers.

Example "laying" processes include wetlaying and drylaying. Example drylaying processes include but are not limited to airlaying, carding, and combinations thereof typically forming layers. Combinations of the above processes yield nonwovens commonly called hybrids or composites. Example combinations include but are not limited to spunbond-meltblown-spunbond (SMS), spunbond-carded (SC), spunbond-airlaid (SA), meltblown-airlaid (MA), and combinations thereof, typically in layers. Combinations which include direct extrusion can be combined at about the same point in time as the direct extrusion process (e.g., spinform and coform for SA and MA), or at a subsequent point in time. In the above examples, one or more individual layers can be created by each process. For instance, SMS can mean a three layer, 'sms' web, a five layer 'ssmms' web, or any reasonable variation thereof wherein the lower case letters designate individual layers and the upper case letters designate the compilation of similar, adjacent layers.

The fibers in a nonwoven web are typically joined to one or more adjacent fibers at some of the overlapping junctions. This includes joining fibers within each layer and joining fibers between layers when there is more than one layer. Fibers can be joined by mechanical entanglement, by chemical bond or by combinations thereof. Fibers can also be joined by heat-bonding, which comprises techniques such as through-air bonding and thermo bonding by use of heated calendar rolls.

Laminates according to the present invention should at least comprise three layers, a first layer (210), a second layer (220) and a third layer (230). These laminates should be useful as backsheets in absorbent articles, namely as backsheet (26) for a diaper (20). Therefore, these laminates are preferably liquid impervious, albeit they preferably are vapor pervious and breathable, at the same time.

The first layer (210) of the laminate (200) is preferably provided from a film, most preferably from a polyolefine film. Suitable materials have been described above in the context of the backsheet (26) of FIG. 1. The second layer (220) is preferably a woven layer or a non-woven layer. Non-woven layers, as described herein above are preferred. The third layer (230) can also be a woven layer or a non-woven layer. The respective woven or non-woven layers can be selected to be hydrophilic or hydrophobic.

Depending on the functionality of the third layer (230), woven layers may be preferred over non-woven layers. For example, when the third layer (230) serves a component of a fastening system, such as the female component, which is often also referred to as the landing zone, a knitted fabric may be suitable. A particularly preferred knitted or knit-type fabric is a wrap-knit weft inserted fabric. In another preferred embodiment of the present invention, a film is provided between the second and third layer (as far as the third layer extends) as to reinforce the third layer. The film is then preferably coextensive with the third layer. Often, also an abrasion resistant fabric or an enforcing fabric may be useful as a third layer.

According to the present invention the third layer (230) is smaller than the second layer (220). Thereby, the third layer (230) will partially, but will not fully cover the adjacent surface of the second layer (220). The position of the third layer (230) in relation to the second layer (220) will depend on the intended use of the laminate (200) or article. In principle, the third layer (230) can be positioned on any part of the surface of the second layer (220). When the third layer (230) is intended to serve as a landing zone of a diaper, comprising the laminate (200) as a backsheet (26), the third layer (230) will preferably only cover the front half of the backsheet (26), even more preferably only the front quarter of the backsheet (26) that is the quarter adjacent to front waist region (36) of the diaper (20).

According to the present invention, the laminate (200) and the absorbent article will comprise indicia (250). The indicia (250) may be provided by printing. According to the present invention, printing may be accomplished by a variety of known printing techniques, such as transfer printing, digital printing, ink or inkjet printing, flexographic printing or the like.

Alternatively, the indicia (250) may be three-dimensional objects, which are attached to the surface of a layer of the laminate (200). The indicia (250), as described further below, have a key function in manufacturing the laminate (200) for the article. After the manufacturing the indicia (250) may still have functional benefits in relation to the use of the laminate (200) or the article. For example the indicia (250) can indicate directions of a high or low abrasion resistance of the third layer (230), or the direction of a high or low friction, of the third layer (230). Alternatively, the indicia (250) may purely serve to indicate the presence of a third layer (230) having functional benefits, as the third layer (230) my otherwise not easily be distinguished from the other layers of the laminate (200).

According to the present invention, the indicia (250) are not provided on any actual surface of any third layer (230), but on another layer, the first layer (210), of the laminate (200). This has multiple benefits: The third layer (230) can be selected without considering the need to provide indicia (250) on the third layer (230). For example, the third layer (230) does not need to provide an outer printable surface. Rather, the outer surface can be optimized in respect to the functionality of the third layer (230), for example abrasive resistance, friction, ability to engage another fastening component. As a further advantage, the indicia (250) are not affected by the interaction of any external components with the third layer (230).

In a further aspect, the layer carrying the indicia (250), the first layer (210), can be optimized regarding the provision of indicia (250), for example a printable layer can be used. In a preferred embodiment of the present invention, the first layer (210) is provided in the form of a polyolefine film. This polyolefine film is suitable to make the laminate (200) liquid impervious. At the same time, the polyolefine film can be readily provided with indicia (250), in particular by printing techniques.

The indicia (250) according to the present invention can comprise a multitude of single indicium elements (240). These elements can be simple geometrical forms like lines, dots, circles, triangle, or squares. These indicium elements (240) can also comprise more complex elements, such as icons or pictures. Such complex elements can be used to convey user instructions, other printed information, manufacturing or trademark information, or alternatively they may also serve decorative purposes.

The indicia (250) are preferably not present over the whole first layer (210), but preferably only in a portion thereof. If the laminate (200) is to be used as to provide a backsheet for an absorbent article, the first indicia (250) are preferably present in the front half of the backsheet, more preferably even in the front quarter of the backsheet.

The multitude of indicium elements (240) will define an outer contour of the first indicia (250). For example the first indicia (250) may have an outer indicia contour in the form of a rectangle. This rectangle may be fully filled; alternatively the indicia (250) may only define the corner stone of such rectangle. Yet alternatively, the indicia (250) may define the complete outer circumference of the rectangle. Of course, the contours of the indicia (250) may also take any other form.

Preferably, the outer contour of the first indicia (250) is chosen in relation to the circumference of the third layer (230). In one preferred embodiment of the present invention, the circumference of the third layer (230) is identical to the outer contour of the first indicia (250). Alternatively, the outer circumference of the third layer (230) may be "similar" to the outer contour of the indicia (250). The term "similar" is used herein in a mathematical sense and denotes that one object has the same shape as another object, but may have a different scale. Therefore, by scaling up or down one object either in the x or y direction, or in both these directions, can be made identical to the other object. For example in accordance with the present invention, the circumference of the third layer (230) may be rectangular. The outer contour of the first indicia (250) can then be provided in the form of a rectangle, which is 10% wider (x-direction) and 10% higher (y-direction) then the rectangle defined by the outer circumference of the third layer (230). Therefore, the indicium elements (240) may be inside the area covered by the third layer or outside and adjacent that area.

While the third layer may carry additional indicia (250) on either of its surfaces, it is preferred that these surfaces do not carry any further indicia.

The first layer, however, may carry second indicia inside or outside the outer contour of the first indicia (250). If first and second indicia comprise mutually different indicia elements, such first and second indicia can readily be distinguished. However, to avoid any such need for distinction, such that the first indicia (250) can even better server their function, it is preferred that no second indicia are present inside the outer contour of the first indicia (250).

According to the present invention the second and third layer (230) together should be translucent. As used herein, translucent refers to layers, which allow for the visibility and distinctiveness of the indicia (250) present on the first layer (210). Any layer will be called translucent if more than 50 of 100 adults aged between 20 and 40 years consider the indicia (250) to be visible and discernable in a representative statistical test set up by a skilled expert in statistical consumer research.

Additionally, Hunter values, L, a, and h, all as describe hereinafter, can be used to further define the translucent property of the layers:

The color and translucency of the second (220) and third layer (230), separately or together, may be measured using the Color Model of the ColorQUEST 45/0 instrumentation available from HunterLab, 11491 Sunset Hills Road, Reston, Va., 22090 USA. See also, The Measurement of Appearance, Hunter, Richard S., Hunter Associates Laboratories, 9529 Lee Highway, Fairfax, Va., 22030 USA. The Color Model describes the color of any material on the basis of three parameters: L, a, and b. "L" is a measure of the lightness of a sample, ranging from L=0 (blackness) to L=100 (whiteness). The quantities "a" and "b" are called opponent-type coordinates. They indicate the degree of redness (positive "a" values), greenness (negative "a" values); and the degree of yellowness (positive "b" values), blueness (negative "b" values). For neutral colors (e.g., white, gray, black), "a" and "b" should be about zero. The higher the values of "a" and "b" for a given sample, the more saturated or chromatic is the color of that sample. For the values referred to herein, the ColorQUEST instrument is used under the conditions of the 2°/D65 international standard and a 2° reflecting angle.

The layers are measured by laying, them onto a green reference sample of L=54.9, a=34.89 and b=19.20. When woven or non-woven or knitted layers, as described herein, are placed onto the sample and thereby cover the sample, it appears less green and more white, in other words, the L value increases (e.g. to 60) and the b value decreases (e.g. to 10). It is preferred that the appearance of the reference sample is impacted as few as possible. The L value of the covered, sample minus the L value of the reference sample is referred to as Hunter $\Delta L$. The b value of the reference sample minus the covered sample is referred to as Hunter $\Delta b$. Therefore the according to the present invention, the second layer and the third layer, each itself and in combination with each other, are preferably translucent in the sense that Hunter $\Delta L$ is less than 30, more preferably less than 25, 20, 15, 10, 8, or 5. It can be preferable that Hunter $\Delta L$ is more than 1, such that the presence of the layers is more easily recognized. Further, according to the present invention, the second layer and the third layer, each itself and in combination with each other, are preferably translucent in the sense that Hunter $\Delta b$ is less than 15, more preferably less than 12, 10, 8, or 5. It can be preferable that Hunter $\Delta b$ is more than 1, such that the presence of the layers is more easily recognized.

It should also be noted, that the indicia (250) provided on the first layer (210) of the laminate (200) or absorbent article preferably are of saturated and chromatic colors. Preferably the indicia elements (240) comprised by the first indicia (250) have dominating red, green or blue colors, and thereby preferably have high positive or negative a-values, preferably with absolute values of more than 10, more preferably of more than 20 or 30, and have high positive, yet more preferably high negative b-values, preferably with absolute values of more than 10, more preferably of more than 15 or 20.

The translucent property of the second and third layer (230), preferably together with a suitable selection of saturated printing colors of the first layer (210), will ensure that the indicia (250) are easily perceived both by optical manufacturing equipment and by a user of the laminate (200) or absorbent article. A particular benefit of such selection is also that no sharp optical contrast exists between indicia (250) covered by the third layer (230) and indicia (250) not covered by the third layer (230), or in other words indicia (250) covered by both the second and third layer (230) versus indicia (250) covered by only the second layer (220). If the indicia (250), for example, comprise text, the text will be much easier to read if all words or letters have about the same intensity. Likewise, a reliable positioning of the third layer (230) will be more readily achieved if indicia (250) can equally well be identified when being detected through the second layer or through the second and the third layer together.

Method of Manufacturing

A method according, to the present invention will comprise the provision of a first, a second and a third layer (230). In a first step, the first and the second layer (220) are combined. In a second step the third layer (230) is combined with the laminate (200) comprising the first and second layer (220). As the third layer (230) will not fully cover the second layer (220), the third layer (230) must be correctly placed onto the second layer (220). Therefore, the method employs and optical placement controller. The optical placement controller will typically comprise a light emitter a light sensor, and a means for information analysis. This means for information analysis normally is computer based and will typically give a signal to the means for combining the third layer (230) with the two other layers. The light emitter may rely on a conventional light source and optical elements, but can also rely on a LASER source. The light sensor will typically comprise a semiconductor sensor, and in most cases a CCD-sensor. The indicia (250) on the first layer (210) of the laminate (200) will contribute to the light reflection, and therefore the indicia (250) can be indicative of the desired position of the third layer (230).

Especially when a conventional or low intensity light source is used, it is important that light is emitted through and reflected through the third layer (230). Especially in the final steps of the positioning, the third layer (230) will be very close to the other layers and thereby it is almost inevitable that reflected light can only be received though the third layer (230). As the ultimate positioning of the third layer (230) largely depends on the final positioning maneuver, the translucent properties of the third layer (230), and also of the second layer (220) are critical. However, it should also be noted that the second layer must be translucent enough as to transmit incoming and reflected light.

The dimensions and values disclosed herein are not to be understood as being strictly limited to the exact numerical values recited, instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising an absorbent core which is covered by a liquid pervious topsheet on the wearer facing side of the core and a liquid impervious backsheet on the garment facing side of the core, the absorbent article having front and rear waist regions and a re-closable fastening system comprising fastening members connected to said rear waist region and a landing zone connected to said front waist region, the liquid impervious backsheet having a longitudinal centerline and a transverse centerline, the transverse centerline defining a front half of the liquid impervious backsheet and a rear half of the liquid impervious backsheet, the front half having a lateral width and a longitudinal length, the liquid impervious backsheet also having a garment-facing side and a wearer-facing side, the liquid impervious backsheet comprising at least three layers, a first layer being comprised by the wearer facing side of the liquid impervious backsheet and a second layer being comprised by the garment facing side of the liquid impervious backsheet, the first layer comprising a wearer-facing surface and a garment facing surface, the garment facing surface of the first layer of the liquid impervious backsheet comprising at least a first indicium, said first indicium being printed on the garment facing surface of the first layer in the front half of the liquid impervious backsheet, the second layer of the liquid impervious backsheet being provided from a woven, non-woven, knitted, or film material, the liquid impervious backsheet comprising a third layer which is provided from a woven fabric, non-woven fabric, knitted fabric, or film, and the third layer being comprised by the front half of the backsheet thereby partially but not fully covering the garment facing surface of the second layer, and being of a third layer shape bounded by edges and having a longitudinal dimension and a lateral dimension, wherein the longitudinal dimension is less than the longitudinal length of the front half and the lateral dimension is less than the lateral width of the front half, wherein the second layer and the third layer together are translucent as to allow that said first indicium comprised by said first layer to be visible through said second layer and said third layer when looking at the absorbent article from the garment facing side of liquid impervious backsheet, and wherein said third layer forms said landing zone, and the third layer overlies the first indicium, or the first indicium at least partially circumscribes the edges of the third layer.

2. An absorbent article according to claim 1 wherein the garment facing surface of the first layer of the liquid impervious backsheet further comprises a second indicium.

3. An absorbent article according to claim 1 wherein said first layer comprises a polyolefin film.

4. An absorbent article according to claim 1 wherein said second layer comprises a nonwoven material and said third layer comprises a knitted material.

5. An absorbent article according to claim 1 wherein said first layer, said second layer and said third layer are joined to form a laminate by an adhesive.

6. An absorbent article according to claim 1 wherein a film layer is comprised between said second layer and said third layer.

7. An absorbent article according to claim 1, wherein said third layer does not early indicia on any of its surfaces.

8. An absorbent article according to claim 1 wherein said fastening member comprises hook elements and said third layer is one of a nonwoven fabric and a knitted fabric.

* * * * *

UNITED STATES PATENT AND TRADEMARK OFFICE
CERTIFICATE OF CORRECTION

| | |
|---|---|
| PATENT NO. | : 8,632,514 B2 |
| APPLICATION NO. | : 13/103486 |
| DATED | : January 21, 2014 |
| INVENTOR(S) | : Sofie Gilberte Snauwaert et al. |

Page 1 of 1

It is certified that error appears in the above-identified patent and that said Letters Patent is hereby corrected as shown below:

In the Claims

Column 14, Line 49 (Claim 7) – delete "early" and insert -- carry --

Signed and Sealed this
Twenty-seventh Day of May, 2014

Michelle K. Lee
*Deputy Director of the United States Patent and Trademark Office*